United States Patent [19]

Wandell

[11] Patent Number: Plant 6,215

[45] Date of Patent: Jul. 5, 1988

[54] GREEN ASH NAMED URBANITE

[76] Inventor: Willet N. Wandell, Rte. 1, Box 286, Oquawka, Ill. 61469

[21] Appl. No.: 819,586

[22] Filed: Jan. 17, 1986

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Tilton, Fallon, Lungmus & Chestnut

[57] ABSTRACT

A new and distinctive variety of *Fraxinus pennsylvanica* lanceolata having shorter internodes, usually less than four inches long on first year stems, tighter crown being pyramidal symmetrical that maintains its shape, by leaflets of dark green above and silvery underneath, by a thicker bark on the trunk and by being disease and insect resistant.

4 Drawing Sheets

BACKGROUND OF THE INVENTION

This new selection of green ash had its origin from seeds collected from the parent tree in 1965 at Danville, Ill., and grown in central Illinois. These seeds were planted and grew seedlings in Wandell Nursery in central Illinois. Propagelus have been produced in my nursery, out-planted and found to duplicate the original tree. This variety was selected from the superior trees of this group and was out-planted by propagating by budding.

DESCRIPTION OF THE DRAWINGS

The photographic prints attached hereto disclose this new variety of *Fraxinus pennsylvanica,* in which:

The first sheet discloses my new variety planted under urban conditions.

The upper photograph of the second sheet discloses the leaves as they appear in late September.

The lower photograph on the second sheet discloses a close-up view of the bark.

The third sheet discloses the tree after leaf fall.

The upper photograph of the fourth sheet discloses a terminal bud.

The lower photograph of the fourth sheet discloses a leaf scar and bud.

The colors shown are photographically reproduced as nearly true as is reasonably possible to obtain by conventional procedures.

DETAILED DESCRIPTION OF THE NEW PLANT

The following is a detailed description of my new variety of *Fraxinus pennsylvanica* based on observations made of plants grown and cultured according to conventional procedures. The color designations are according to The R.H.S. Colour Chart published in collaboration with The British Colour Council at London, England, except where color terms of dictionary significance are obvious.

THE PLANT

Origin: Seedling.

Parentage: A tree propagated from seeds collected from a parent tree in Danville, Ill.

Classification: *Fraxinus pennsylvanica* variety of *pennsylvanica.*

Form: Moderate sized pyramidal shape.

Height: 35 feet.

Shape: Moderately pyramidal in outline.

Growth: Abundant with a straight trunk and spreading ascending branches. The crown is dense, compact pyramidal in outline. Moderately fast growing at the rate of 18 to 24 inches per year.

Branches: Stout, internodes quite short, 1 to 4 inches long, the first year shoots and leaders 3/16 to ⅝ inch in diameter, green, velutinous; leaf scars semicircular with a flat top, the bundle traces numerous, forming an unclosed C-shaped ring.

Winter buds: Terminal, axillary, and superposed buds present, all sessile, more or less globose or laterally compressed, scurfy scales, medium to dark ferrugineous, covered by 2 to 3 pairs of opposite bud scales.

Shape of leaf: Opposed, 4-ranked odd-pinnately compound with usually 9 leaflets, leaf stalklet length is about 3 inches to about 4¾ inches, petiolate, deciduous.

Leaflets: Dark Green, RHS 136!-A, above and silvery below during growing season, ovate, 3½ to 7 inches long and 1½ to 2¾ inches wide (the lower leaflets smaller), glabrous above and sparsely pubescent below, the apices acuminate, the margins entire with no conspicuous teeth, the bases rounded, often oblique, slightly decurrent on the short petiolules.

Flowers: None observed, plants believed to be sterile.

Disease resistance: Resistant to disease and insects.

Bark: Thicker than usual for the species, grayer-brown in color, with narrow flat-topped, irregular, longitudinal ridges which are transversely broken and confluent and enclose diamond-shaped furrows.

Pubescence: Branched stalk and stalklet pubescence velutinous.

The advantages of this new variety are (1) shorter internodes, usually less than four inches long on first year stems and hence a tighter crown than other trees of the species which usually have internodes 6 to 8 inches or more in length: (2) the pyramidal symmetrical crown that maintains its shape instead of the rounded crown that becomes very irregular on other trees of the species; (3) the leaflets that are thicker and more resistant to tattering than other trees of the species; (4) the consistent color of the leaflets that are lustrous dark green above and silvery below instead of variable shades in other varieties of the species; (5) the thicker bark on the trunk that makes young plants less susceptible to sun scalding; and (6) its apparent disease and insect resistance.

I claim:

1. A new and unique variety of green ash or *Fraxinus pennsylvanica* lanceolata variety of *pennsylvanica* named Urbanite substantially described and illustrated herein characterized in that it differs from other varieties of the same species by the unique combination of shorter internodes, usually less than four inches long on first year stems, by the tighter, pyramidal symmetrical crown that maintains its shape, by the consistent color of the leaflets that are lustrous dark green above and silvery below, by the thicker bark on the trunk that makes young plants less susceptible to sun scalding, and by its apparent disease and insect resistance.

* * * * *

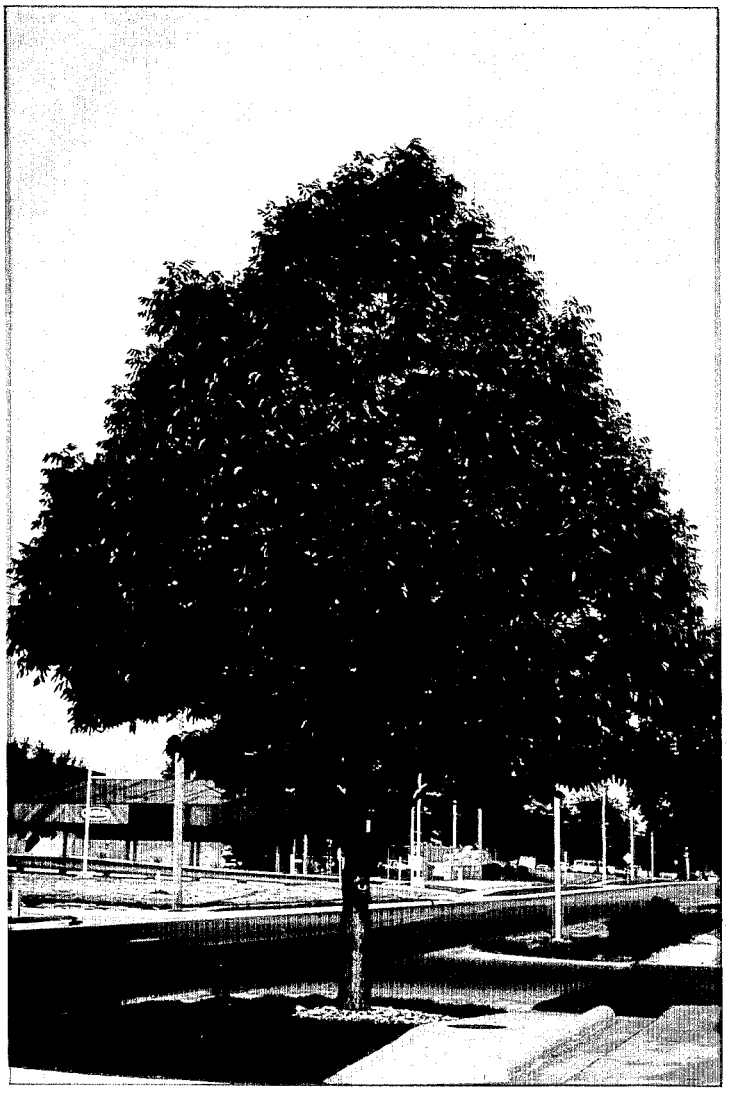

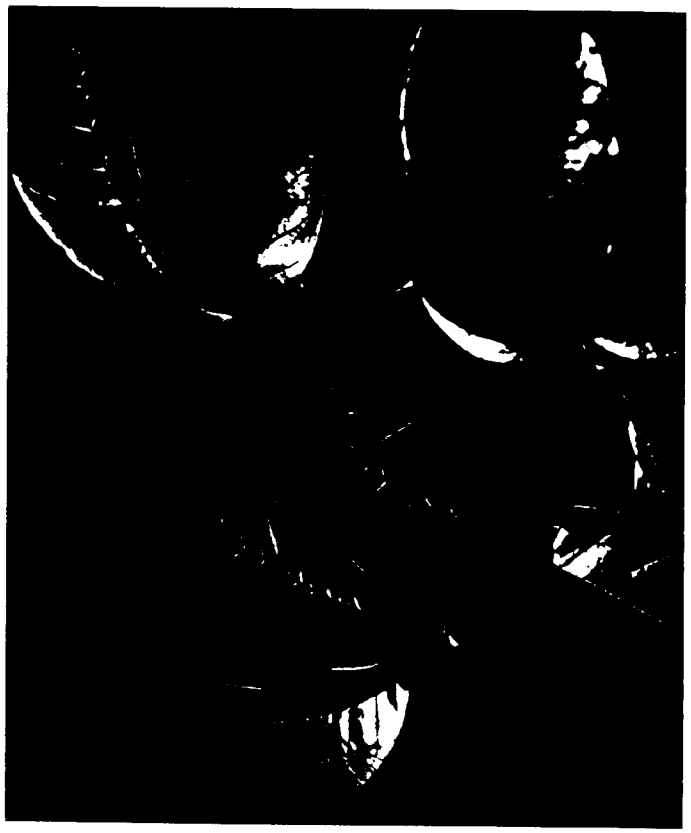
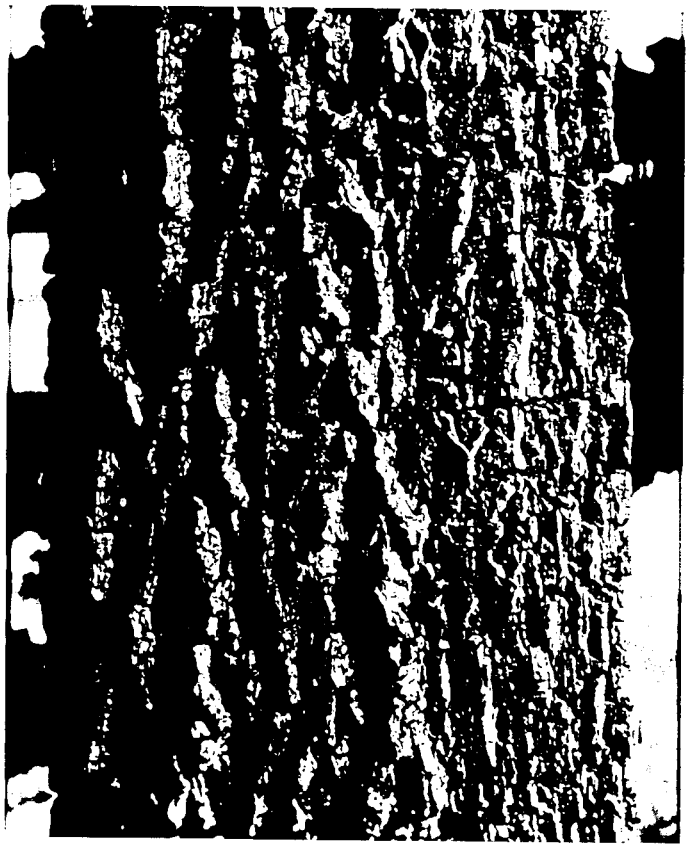

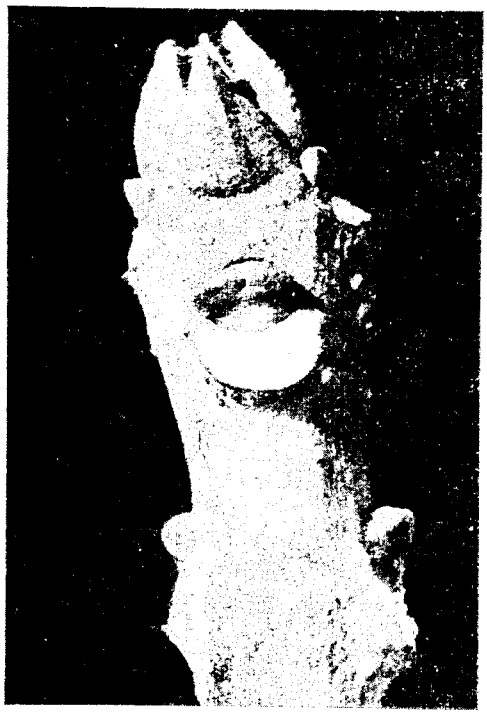
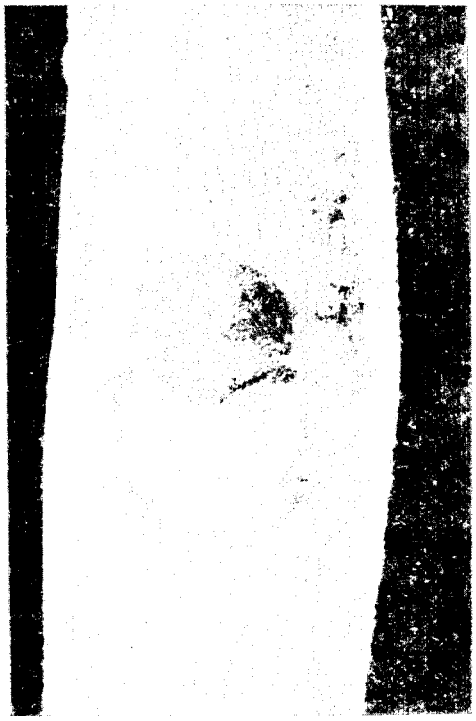

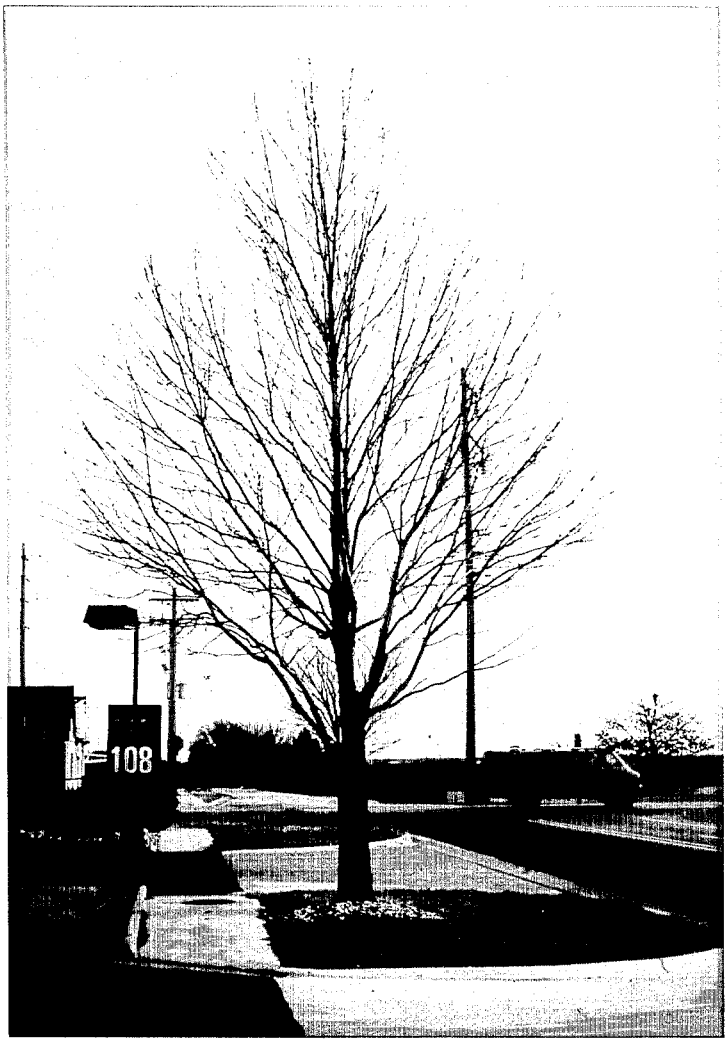
108